United States Patent [19]
Enders et al.

[11] 3,978,222
[45] Aug. 31, 1976

[54] FUNGICIDALLY ACTIVE 3-AMINO-PROPIONIC ACID CHLOROANILIDES

[75] Inventors: Edgar Enders, Cologne; Paul-Ernst Frohberger, Leverkusen, both of Germany

[73] Assignee: Bayer Aktiengesellschaft, Leverkusen, Germany

[22] Filed: Feb. 5, 1975

[21] Appl. No.: 547,418

Related U.S. Application Data

[63] Continuation-in-part of Ser. No. 359,166, May 10, 1973, Pat. No. 3,879,539.

[30] Foreign Application Priority Data

May 17, 1972 Germany............................ 2224006

[52] U.S. Cl............................ 424/267; 260/293.76; 260/293.77; 260/326.8; 424/274
[51] Int. Cl.² ............................................ A01N 9/22
[58] Field of Search ........................... 424/267, 274; 260/293.76, 293.77, 326.8

[56] References Cited
UNITED STATES PATENTS
2,576,106  11/1951  Cusik .................................. 260/561

OTHER PUBLICATIONS
Mel'Nikov et al., – Zh. Org. Khim. (U.S.S.R.), pp. 96–103 (1968).

*Primary Examiner*—Leonard Schenkman
*Attorney, Agent, or Firm*—Burgess, Dinklage & Sprung

[57] ABSTRACT

Compositions and methods of using 3-amino-propionic acid chloroanilides of the formula

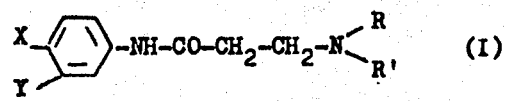

in which
X and Y are each halogen, methyl or trifluoromethyl, provided that at least one of them is halogen,
R is alkyl, cycloalkyl or alkenyl of up to 7 carbon atoms, and
R' is hydrogen, or alkyl or alkenyl of up to 6 carbon atoms, or
R and R' conjointly form an alkylene group of 4 or 5 carbon atoms which forms a ring with the nitrogen atoms to which R and R' are attached, some of which are new, which possess strong fungicidal, bactericidal, insecticidal and bird-repellent properties.

5 Claims, No Drawings

FUNGICIDALLY ACTIVE 3-AMINO-PROPIONIC ACID CHLOROANILIDES

This application is a continuation-in-part of application Ser. No. 359,166, filed May 10, 1973, now U.S. Pat. No. 3,879,539.

The present invention relates to and has for its objects the provision of particular new active compositions in the form of mixtures with solid and liquid dispersible carrier vehicles of certain 3-amino-propionic acid chloroanilides, some of which are new, and which possess valuable strong fungicidal, microbicidal, insecticidal and bird-repellent properties, and methods for using such compounds in a new way, especially for combating and controlling fungi, microbes, insects and harmful birds with other and further objects becoming apparent from a study of the within specification and accompanying examples.

As has been known for a long time, zinc ethylene-1,2-bis-dithiocarbamate (Compound A) is used as a fungicide in agriculture and in horticulture; the said compound is of great importance amongst commercially available products (see R. Wegler, "Chemie der Pflanzenschutz- and Schädlingsbekämpfungsmittel" ("Chemistry of Plant Protection Agents and Pesticides"), volume 2, page 65, Berlin/Heidelberg/New York (1970)). However, the action is not always satisfactory if low concentrations are used.

It has now been found that the 3-amino-propionic acid anilides of the general formula

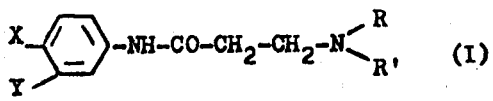

in which
X and Y are each halogen, methyl or trifluoromethyl, provided that at least one of them is halogen,
R is alkyl, cycloalkyl or alkenyl of up to 6 carbon atoms, and
R' is hydrogen, or alkyl or alkenyl of up to 6 carbon atoms, or
R and R' conjointly form an alkylene group of 4 or 5 carbon atoms, which forms a ring with the nitrogen atom to which R and R' are attached,
as well as their acid-addition salts, display strong fungicidal properties.

Preferably, X and Y are each chlorine, bromine, methyl or trifluoromethyl, R is alkyl of up to 6 carbon atoms, cyclopentyl, cyclohexyl or lower alkenyl of 3 or 4 carbon atoms, and R' is hydrogen or lower alkyl or alkenyl with, in either case, up to 4 carbon atoms, or R and R', together with the linking nitrogen atoms, form a pyrrolidine or piperidine ring system.

Surprisingly, the 3-amino-propionic acid anilides which can be used according to the invention, as well as their acid-addition salts, display a substantially greater fungicidal action than zinc ethylene-1,2-bis-dithiocarbamate, which is known from the state of the art. The present invention thus represents an enrichment of the art.

A number of the compounds which can be used according to the invention are already known (see USSR Patent Specification No. 233,683). Compounds which have not been described in the literature can be produced either by reacting 3-chloropropionic acid anilides with excess primary or secondary amine at temperatures between +20°C and the boiling point of the amine used, or by adding primary or secondary amines to acrylic acid anilides within the aforesaid temperature range. In the reactions mentioned, diluents, such as alcohols (for example, methanol and ethanol), ketones (for example, acetone) or hydrocarbons (for example, benzene and toluene) can also be employed. After completion of the reaction, and after distilling off the excess amine and, if relevant, the solvent, the reaction product can be isolated as the free base after stirring with aqueous caustic alkali solution, or as the hydrochloride after recrystallization from dilute hydrochloric acid. Both the free bases and the acid-addition salts can be employed for the end use according to the invention.

The active compounds according to the invention, as stated above, show a strong fungitoxic action. They do not damage crop plants in the concentrations required for combating fungi and have only a low toxicity to warm-blooded animals. For these reasons they are suitable for use as plant-protection agents, to combat fungi. Fungitoxic agents are employed in plant protection for combating Archimycetes Phycomycetes, Ascomycetes, Basidiomycetes and *Fungi Imperfecti*.

The active compounds are especially suitable for use as seed dressings and also for the treatment of soil. Herein, their action is primarily directed against seed-borne fungi and phytophathogenic soil fungi; in particular, there may be mentioned bunt diseases of cereals, such as bunt of wheat and loose smuts of oats and also helminthosporioses of barley and of oats, for example, stripe diseases of barley, as well as diseases of seedlings, for example in cereals, maize, pulses or cotton, caused by fungi of, for example, the genera Rhizoctonia or Fusarium.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkenes (e.g. cyclohexane, etc.), paraffins (e.g. petroleum or mineral oil fractions), chlorinated aliphatic hydrocarbons (e.g. methylene chloride, chlorethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alimina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other fungicides, microbicides, insecticides and bird repellents, or acaricides, rodenticides, bactericides, nematocides, herbicides, fertilizers, growth-regulating agents, etc., if desired, or in the form of particular dosage preparations for specific application made therefrom, such as solutions, emulsions, suspensions, powders, pastes and granules, which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprises mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

In dressing, amounts of active compound of 50 mg to 50 g, preferably of 200 mg to 10 g, are in general employed per kilogram of seed.

In the treatment of soil, which can be carried out by overall, band or spot application, concentrations of 1 to 1,000 g of active compound per cubic meter of soil, preferably 10 to 200 g per cubic meter, are generally required at the place of the intended effect.

Furthermore, the present invention contemplates methods of selectively killing, combating or controlling pests, e.g. fungi, bacteria, insects and harmful birds, and more particularly methods of combating fungi, which comprises applying to at least one of correspondingly (a) such fungi, (b) such bacteria, (c) such insects, and (d) the corresponding habitat thereof or of harmful birds, i.e. the locus to be protected, a correspondingly combative or toxic amount, i.e. a fungicidally, bactericidally, insecticidally or bird-repellent effective amount, of the particular active compound of the invention alone or together with a carrier vehicle as noted above. The instant formulations or compositions are applied in the usual manner, for instance by spraying, atomizing, vaporizing, scattering, dusting watering, squirting, sprinkling, pouring, fumigating, dry dressing, slurry dressing, moist dressing, wet dressing, and the like.

It will be realized, of course, that the concentration of the particular active compound utilized in admixture with the carrier vehicle will depend upon the intended application. Therefore, in special cases it is possible to go above or below the aforementioned concentrated ranges.

The synthesis, unexpected superiority and outstanding activity of the particular new compounds of the present invention are illustrated, without limitation, by the following examples:

EXAMPLE 1

Seed dressing test/bunt of wheat (seed-borne mycosis)

To produce a suitable dry dressing, the active compound was extended with a mixture of equal parts by weight of talc and kieselguhr to give a finely powdered mixture with the desired concentration of the active compound.

Wheat seed was contaminated with 5 g of the chlamydospores of *Tilletia caries* per kg of seed. To apply the dressing, the seed was shaken with the dressing in a closed glass flask. The seed, on moist loam under a cover of a layer of muslin and 2 cm of moderately moist compost soil, was exposed to optimum germination conditions for the spores for 10 days at 10°C in a refrigerator.

The germination of the spores on the wheat grains, each of which was contaminated with about 100,000 spores, was subsequently determined microscopically. The smaller the number of spores which had germinated, the more effective was the active compound.

The active compounds, the concentrations of the active compounds in the dressing, the amounts of dressing used and the percentage spore germination can be seen from the following Table 1:

Table 1
Seed dressing test/bunt of wheat
| Active compound | Active compound concentration in the dressing, in % by weight | Amount of dressing used in g/kg of seed | Spore germination in % |
|---|---|---|---|
| without dressing | — | — | >10 |
| 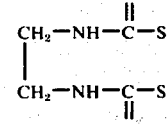 (known) (A) | 10 | 1 | 5 |
| 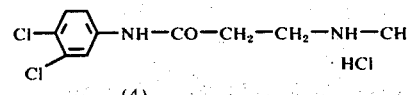 (4) | 10 | 1 | 0.05 |
| 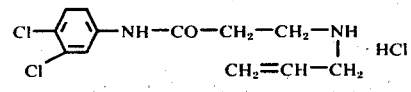 (2) | 10<br>3<br>1 | 1<br>1<br>1 | 0.000<br>0.005<br>0.05 |
| 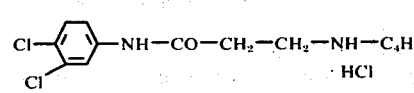 (5) | 10 | 1 | 0.5 |
| 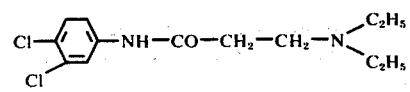 (3) | 10<br>3 | 1<br>1 | 0.000<br>0.005 |
| 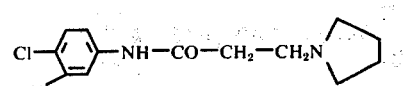 (7) | 10 | 1 | 0.000 |
| 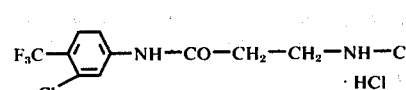 (8) | 10<br>3<br>1 | 1<br>1<br>1 | 0.000<br>0.005<br>0.5 |
| 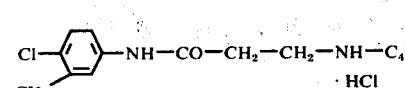 (9) | 10 | 1 | 0.5 |
| 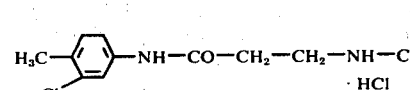 (10) | 10 | 1 | 0.05 |
| 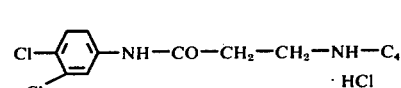 (6) | 10<br>3 | 1<br>1 | 0.005<br>0.05 |
| 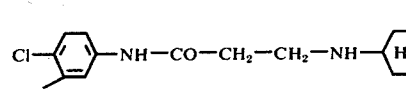 (1) | 10<br>3 | 1<br>1 | 0.005<br>0.05 |

The production of the compounds used in this invention is illustrated by the following Examples.

EXAMPLE 2

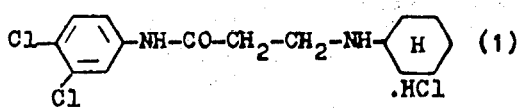

50 g of 3-chloropropionic acid 3,4-dichloroanilide were introduced into 200 g of cyclohexylamine and the mixture was stirred for 3 hours at 80°C. Thereafter, the cyclohexylamine was distilled off in vacuo and the residue was recrystallized from a large amount of water with the addition of a little hydrochloric acid. 59 g of 3-cyclohexylaminopropionic acid 3,4-dichloroanilide hydrochloride of melting point 249°–251°C were obtained.

EXAMPLE 3

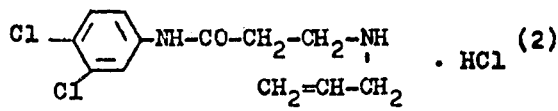

50 g of 3-chloropropionic acid 3,4-dichloroanilide were introduced into 180 g of allylamine and the mixture was stirred for one hour at 20°C and thereafter for one hour under reflux. The allylamine was then distilled off and the residue was recrystallized from dilute hydrochloric acid. 50 g of 3-allylamino-propionic acid 3,4-dichloroanilide hydrochloride of melting point 194°–195°C were obtained.

EXAMPLE 4

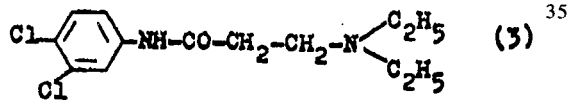

1,000 g of 3-chloropropionic acid 3,4-dichloroanilide were introduced into 1,000 g of diethylamine over the course of 15 minutes and the mixture was stirred for one hour at 20°C and one hour under reflux. Thereafter the excess diethylamine was distilled off and the residue was stirred with 500 ml of water. The product was filtered off, washed with water and recrystallized from dilute methanol. 1,095 g of 3-diethylamino-propionic acid 3,4-dichloroanilide of melting point 65°–67°C were obtained.

The following compounds of the general formula (I) were produced by methods analogous to those above:

Other compounds which may be similarly prepared and employed include:
3-diallylamino-propionic acid 3-fluoro-4-trifluoromethylamide,
3-dimethylamino-propionic acid 3,4-dibromoanilide, and the like.

It will be appreciated that the instant specification and examples are set forth by way of illustration and not limitation, and that various modifications and changes may be made without departing from the spirit and scope of the present invention.

What is claimed is:

1. A method of combating phytopathogenic fungi which comprises applying to said pest or its habitat a phytopathogenic fungicidally effective amount of a 3-aminopropionic acid anilide of the formula

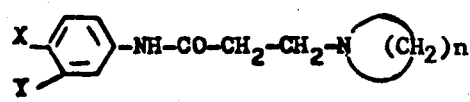

in which
X and Y are each halogen, methyl or trifluoromethyl, provided that at least one of them is halogen, and
$n$ is 4 or 5,
or an acid-addition salt thereof.

2. The method according to claim 1, in which X and Y are each chlorine, bromine, methyl or trifluoromethyl.

3. The method according to claim 1, wherein said anilide is 3-pyrrolidine-propionic acid 3,4-dichloroanilide of the formula

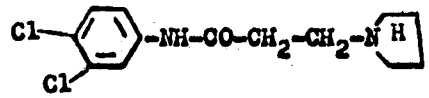

4. The method according to claim 1, wherein said anilide is 3-piperidino propionic acid 3,4-dichloroanilide of the formula

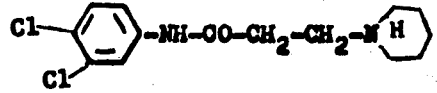

5. A phytopathogenic fungicidal composition comprising a phytopathogenic fungicidally effective

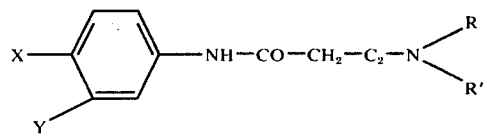

| Compound No. | X | Y | R | R' | Properties |
|---|---|---|---|---|---|
| 4 | Cl | Cl | $CH_3$ | H | Hydrochloride, melting point 165–168°C |
| 5 | Cl | Cl | $C_4H_9$ | H | Hydrochloride, melting point 194–196°C |
| 6 | Cl | Cl | $C_4H_9$-(i) | H | Hydrochloride, melting point 197–198°C |
| 7 | Cl | Cl | —$(CH_2)_4$— | | Hydrochloride, melting point 195–198°C |
| 8 | $CF_3$ | Cl | $C_4H_9$ | H | Hydrochloride, melting point 207–209°C |
| 9 | Cl | $CH_3$ | $C_4H_9$ | H | Hydrochloride, melting point 208–210°C |
| 10 | $CH_3$ | Cl | $C_4H_9$ | H | Hydrochloride, melting point 214–216°C |
| 11 | Cl | Cl | —$(CH_2)_5$— | | Free base melting point 90–92°C | amount of a 3-aminopropionic acid anilide of the formula
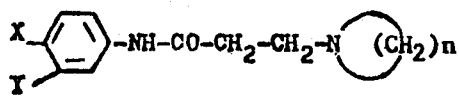
in which
X and Y are each halogen, methyl or trifluoromethyl, provided that at least one of them is halogen, and
n is 4 or 5,
or an acid-addition salt thereof, in admixture with a diluent.
* * * * *